(12) United States Patent
Ko et al.

(10) Patent No.: US 10,980,742 B2
(45) Date of Patent: Apr. 20, 2021

(54) NANO-CRYSTALLIZED HERBAL INGREDIENT-CONTAINING PACKAGE AND METHOD OF PREPARING HERBAL DECOCTION

(71) Applicant: Nano and Advanced Materials Institute Limited, Hong Kong (HK)

(72) Inventors: Chun Hay Ko, Hong Kong (HK); Connie Sau Kuen Kwok, Hong Kong (HK); Chun Fai Ng, Hong Kong (HK); Ka Man Tse, Hong Kong (HK); Ying Ying Ng, Hong Kong (HK)

(73) Assignee: Nano and Advanced Materials Institute Limited, Hong Kong (HK)

( * ) Notice: Subject to any disclaimer, the term of this patent is extended or adjusted under 35 U.S.C. 154(b) by 5 days.

(21) Appl. No.: 16/485,790

(22) PCT Filed: Jan. 17, 2019

(86) PCT No.: PCT/CN2019/072088
§ 371 (c)(1),
(2) Date: Aug. 14, 2019

(87) PCT Pub. No.: WO2019/141204
PCT Pub. Date: Jul. 25, 2019

(65) Prior Publication Data
US 2020/0046640 A1 Feb. 13, 2020

Related U.S. Application Data

(60) Provisional application No. 62/709,338, filed on Jan. 17, 2018.

(51) Int. Cl.
| | | |
|---|---|---|
| *B65D 85/804* | (2006.01) | |
| *A61K 9/00* | (2006.01) | |
| *A23L 33/105* | (2016.01) | |
| *A61K 36/076* | (2006.01) | |
| *A61K 36/488* | (2006.01) | |
| *A61K 36/815* | (2006.01) | |
| *A61K 9/14* | (2006.01) | |
| *A61K 9/19* | (2006.01) | |
| *A61K 9/51* | (2006.01) | |
| *A61K 36/236* | (2006.01) | |
| *A61K 36/537* | (2006.01) | |
| *A61K 36/725* | (2006.01) | |
| *A61K 36/734* | (2006.01) | |

(52) U.S. Cl.
CPC .......... *A61K 9/0095* (2013.01); *A23L 33/105* (2016.08); *A61K 9/146* (2013.01); *A61K 9/19* (2013.01); *A61K 9/51* (2013.01); *A61K 9/5138* (2013.01); *A61K 36/076* (2013.01); *A61K 36/236* (2013.01); *A61K 36/488* (2013.01); *A61K 36/537* (2013.01); *A61K 36/725* (2013.01); *A61K 36/734* (2013.01); *A61K 36/815* (2013.01); *B65D 85/8043* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 4,765,500 A | * | 8/1988 | Ingram | .............. B65D 11/1886 220/4.24 |
| 9,987,322 B1 | * | 6/2018 | Berry | ..................... A61K 45/06 |
| 2005/0047985 A1 | * | 3/2005 | Mori | .................... C01B 33/1585 423/335 |
| 2019/0321430 A1 | * | 10/2019 | Shraibom | .............. A61K 47/10 |

FOREIGN PATENT DOCUMENTS

| CN | 105982877 | * | 10/2016 | ............... A61K 9/48 |
|---|---|---|---|---|
| KR | 101604090 | * | 3/2016 | ............... A61K 9/16 |

OTHER PUBLICATIONS

KR101604090 Eng Tran. Published: Mar. 2016.*
CN105982877 Eng Tran. Published: Oct. 2016.*

* cited by examiner

*Primary Examiner* — David J Blanchard
*Assistant Examiner* — Lori K Mattison
(74) *Attorney, Agent, or Firm* — Idea Intellectual Limited; Margaret A. Burke; Sam T. Yip

(57) ABSTRACT

The present invention provides a nano-crystallized herbal ingredient-containing package for use in a food processor or being used directly to prepare a herbal decoction. The package includes a housing; single or multiple herbal ingredient nano-crystals; one or more non-additive and anti-caking spacers for preventing caking that blocks solvent flowing through the package towards the single or multiple herbal ingredient nano-crystals during processing by the food processor; and optionally one or more stabilizing agents for stabilizing the single or multiple herbal ingredient nano-crystals during nano-crystallization of the herbal ingredients and during preparation of the herbal decoction. A method of preparing a herbal decoction from the package is also provided.

19 Claims, 10 Drawing Sheets

NANO-CRYSTALLIZED HERBAL INGREDIENT-CONTAINING PACKAGE AND METHOD OF PREPARING HERBAL DECOCTION

CROSS-REFERENCE TO RELATED APPLICATION

This application is a 371 application of an International Patent Application number PCT/CN2019/072088 filed Jan. 17, 2019, which claims priority from the U.S. provisional patent application Ser. No. 62/709,338 filed Jan. 17, 2018, and the disclosures of which are incorporated herein by reference in their entirety.

FIELD OF THE INVENTION

The present invention relates to a nano-crystallized herbal ingredient-containing package. The present invention also relates to a method of preparing herbal decoction from the nano-crystallized herbal ingredient-containing package within a relatively shorter period of time than the conventional way of preparing herbal decoction from the herbal ingredients.

BACKGROUND

Traditionally, Traditional Chinese Medicine (TCM) is administrated in a form of decoction, in which several herbs are boiled in water for about an hour, and the remaining concentrated liquid is used for consumption for better health management. However, traditional decoctions have some disadvantages to users, such as (i) difficulties in ensuring quality of the herbal ingredients, (ii) hour-long time required to prepare, (iii) inconvenience in transportation and storage of liquid. Historically, different kinds of formulations have been developed in response to these shortcomings. These strategies include traditional preparations of wan (pills), san (powder) and the modern formulations of granules. In recent years, some Chinese pharmaceutical companies have developed more than 600 kinds of individual herb granules and 200 kinds of herbal formulae, which have been widely used in clinical practice. Nevertheless, there are more evidences demonstrating that contents of constituents in an herbal decoction prepared in a traditional way with boiling may be different from those found in an identical physical mixture of granules [1,2]. It is postulated and widely accepted that some other new compounds are to be generated from herb-herb interactions during the boiling process. Therefore, the health beneficial effects generating from the conventional TCM decoction boiling method cannot be simply physically replaced by a mixture of individual ingredient granules.

Nowadays, the commercial coffee capsule has revolutionized coffee drinking habit from the old days. Development of a convenient way to get TCM decoction from a food processor for preparing a freshly brewed coffee using coffee capsule such as from a single-serve brewer is attractive. Users can prepare their own cup of herbal decoction from herbal ingredient-containing capsule within a minute. However, technical difficulties in limited dissolution rate may hinder the development of herbal decoction capsule because many herbal ingredients are poorly soluble or even insoluble in water. Raw or coarse herbal materials or even granule form of herbal extract have not had enough surface area for contact with the solvent during brewing, which lengthens the preparation time and limits the number and/or type of herbal ingredients to be used for preparing an herbal decoction.

Nanocrystals, a carrier-free colloidal delivery system in nano-sized range, is a decent approach to solve these difficulties by reducing the ingredient's particle size, thus enhancing the dissolution rate and the solubility as well [3]. For example, the Chinese patent CN103211759B disclosed a formulation which is a carrier free colloidal system and contains a stabilizer preferably selected from hydroxypropyl methyl cellulose. The preparation process disclosed in that Chinese patent appears to apply ball milling and spray drying techniques to obtain nano-crystalline particulate. Another example is the Chinese published patent application CN102895451A which disclosed a broad-spectrum anti-viral nano-sized traditional Chinese medicine including herbal extracts from *Salvia* miltiorrhiza. The preparation process disclosed in the second example also appears to apply ball milling and spray drying techniques to obtain nano-crystalline particulate of the herbal extracts. However, none of these examples provides a means for extracting or eluting the herbal ingredients from the nano-crystalline particulate in a more efficient way like the use of conventional single-serve coffee capsule to prepare a coffee from a coffee machine. Therefore, a convenient yet cost- and time-effective means to prepare an herbal decoction while the potential herb-herb interactions generated in the TCM decoction is preserved is utmost needed.

SUMMARY OF THE INVENTION

Accordingly, a first aspect of the present invention relates to a package including single or multiple herbal ingredients which are nano-crystallized from their corresponding natural source(s) in the absence of using any solvent for extraction, one or more non-additive and anti-caking spacers, and optionally one or more stabilizing agents that are food-safe and do not attribute to the functional properties of the resultant herbal decoction.

In one embodiment, the package is a container including at least a side wall, a top wall and a bottom wall forming a cavity for housing said single or multiple nano-crystallized herbal ingredients, one or more non-additive and anti-caking spacers, and optionally one or more stabilizing agents. The housing can be made of polymer, metal and/or an alloy thereof.

In another embodiment, the package is configured for a food processor to brew said single or multiple nano-crystallized herbal ingredients in the presence of a solvent in order to prepare an herbal decoction. The food processor can be a specially designed machine for said package or any commercially available food or beverage making machine.

In other embodiment, the package is configured such that said single or multiple nano-crystallized herbal ingredients are directly dissolved into or diffused from an internal porous structure of the package into a solvent. The internal porous can be made of polymers and/or fibers such as cellulose.

In yet another embodiment, said single or multiple nano-crystallized herbal ingredients are generated by ultrafine grinding and/or high-pressure pulverization with or without said one or more stabilizing agents.

In an exemplary embodiment, said single or multiple nano-crystallized herbal ingredients have an average particle size of equal to or less than about 1,000 nm; said one or more non-additive and anti-caking spacers have an average particles size of about 0.5 to 5 mm. Preferably, said one or more non-additive and anti-caking spacers have an average particle size of about 1 to 3 mm.

In one embodiment, the weight percentage of different components in the present package is as follows: about 5-50 wt. % of said single or multiple nano-crystallized herbal ingredients; about 45-90 wt. % of said one or more non-additive spacers; about 0-5 wt. % of said one or more stabilizing agents.

In other embodiment, said single or multiple nano-crystallized herbal ingredients comprise: nano-crystals of part of flower, leaves, seed, fruit stem, root and/or rhizome of species under kingdom Plantae; and/or nano-crystals of part of cap, stalk, hyphae, and/or spores of species under kingdom Fungi.

In another embodiment, said single or multiple nano-crystallized herbal ingredients comprise nano-crystals of any Chinese herbal medicine listed in Chinese Pharmacopeia.

In certain embodiments, said single or multiple herbal ingredient nano-crystals are prepared by ultrafine grinding or high-pressure pulverisation of the corresponding raw or coarse herbal materials.

In yet another embodiment, said single or multiple nano-crystallized herbal ingredients comprise water-soluble, poorly water-soluble and/or water-insoluble herbal ingredients.

In other embodiment, said one or more non-additive and anti-caking spacers comprise natural and synthetic materials. Preferably, said natural material comprises one or more of sesame, millet and/or quinoa; said synthetic material comprises one or more of amorphous silica, and/or zirconium oxide in any form such as bead or powder.

In one embodiment, said one or more stabilizing agents comprise ionic and/or non-ionic stabilizing agents. Preferably, said ionic stabilizing agents comprise sodium carboxymethylcellulose, sodium lauryl sulfate, and/or dioctyl sodium sulfosuccinate; said non-ionic stabilizing agents comprise poly(vinyl) alcohol, D-alpha-tocopheryl polyethylene glycol succinate, pectin, and/or hydroxypropylmethyl cellulose.

Another aspect of the present invention relates to a method of preparing an herbal decoction from the package of the present invention. The method includes providing a flow of solvent under an elevated pressure and at an elevated temperature to said package such that the solvent flows through an opening of the package towards the nano-crystals of said single or multiple nano-crystallized herbal ingredients in order to process or brew for a first period of time, or providing a solvent under atmospheric pressure and at an elevated temperature to said package for a second period of time until said solvent substantially dissolves all the nano-crystals of said single or multiple nano-crystallized herbal ingredients to result in the herbal decoction.

In an exemplary embodiment, the solvent is provided at about 75 to 100° C.

In one embodiment, the flow of solvent is provided by a food processor under the elevated pressure and at the elevated temperature to said package. Preferably, the opening of the package is created at the time when said flow of solvent is provided by said food processor. The elevated pressure is about 1.01325 to 20 bars.

In another embodiment, the solvent is provided under the atmospheric pressure and at the elevated temperature of about 75 to 100° C. until the nano-crystals of the single or multiple nano-crystallized herbal ingredients are substantially dissolved into said solvent. In this embodiment, the nano-crystals of said single or multiple nano-crystallized herbal ingredients may be diffused from said package through a porous structure or directly dissolved into the solvent by means of mixing the same with the solvent in a container. By this way, the time duration for the second period of time the nano-crystals are substantially dissolved into the solvent is much longer than that for processing or brewing the nano-crystals under the elevated pressure. Preferably, the second period of time is about 10 to 20 times longer than the first period of time according to the present method. More preferably, the first period of time is equal to or less than a minute, while the second period of time is about 10 to 20 minutes in order to have the herbal decoction prepared according to the present method.

BRIEF DESCRIPTION OF THE DRAWINGS

Embodiments of the present invention are described in more detail hereinafter with reference to the drawings, in which.

DEFINITIONS

Figure 1:
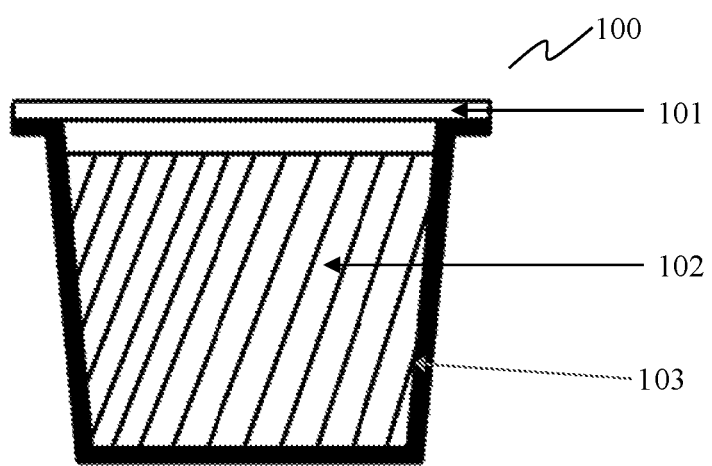
FIG. 1 shows a schematic diagram of an herbal ingredient-filled capsule in accordance with an embodiment of the present invention.

The term "non-additive" is used herein to define the nature of a material, component or ingredient that does not attribute to or modify any physical and/or functional properties such as taste, flavour, color, acidity, viscosity, etc., of the food or beverage prepared from the composition containing the active ingredients of the intended food or beverage;

The term "anti-caking" is used herein to define a functional aspect of a material, component or ingredient that attributes to the effect of preventing the active ingredients of the intended food or beverage from congealing into a solid mass and blocking a solvent flowing through the active ingredients during processing or brewing by a food processor.

The term "spacer" used herein refer to a material, component or ingredient that aids the separation of the active ingredients of the intended food or beverage during processing or brewing by a food processor and/or creates space between each of the nano-crystals of the active ingredients or between each nano-crystal and other component in the composition for preparing the intended food or beverage.

The phrase "food processor" used herein refers to any processor for food and/or beverage that can be controlled manually, semi-automated, or fully automated such that the intended food or beverage is prepared from the composition containing the active ingredients. Example of the food processor includes but not limited to any specially designed food processor for the present invention and commercially available beverage making machine such as coffee making machine for brewing coffee from single-serve coffee capsule containing the essential coffee ingredients.

The term "package" used herein includes but not limited to any enclosures comprising at least a side wall, a bottom wall and a top wall such as a capsule, cartilage, pod, bag, container in any three-dimensional structure, etc. The package is not only limited to be used in a specially designed or conventional food processor but also in any other possible container containing a solvent of interest for extracting, eluting and/or dissolving the active ingredient(s) of the intended food or beverage from the package.

The term "nano-crystal" used herein refers to a material, component or ingredient with at least one dimension smaller than 1,000 nanometres which aids the release rate and/or extraction yield of the active ingredients during processing or brewing by a food processor for preparing the intended food or beverage.

It should be apparent to those skilled in the art that many modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "includes", "including", "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

DETAILED DESCRIPTION

The following description and the corresponding embodiments are set forth as preferred examples. It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

FIG. 1 provides a schematic diagram of an example of the package for housing the nano-crystals of the herbal ingredients and other necessary components to be readily processed or brewed by the food processor for preparing an herbal decoction according to an embodiment of the present invention. In this example, the package is a capsule-like structure (100) including a top wall (101), and side and bottom walls (103) forming a cavity for housing the nano-crystals of the herbal ingredients and other components (102). Any of the top, side and bottom walls can be made of a polymer, metal and/or any metal alloy, e.g., aluminum. It should be understood that the package for the present invention is not limited to the capsule-like structure as shown in FIG. 1 but also includes cartilage, pod, bag, and container in any three-dimensional shape. Optionally, an internal porous structure (not shown in FIG. 1) which can be made of polymers and/or fibers, e.g., cellulose, is incorporated into the package, depending on the food processor and/or the method of preparing the herbal decoction.

EXAMPLES

Figure 2:
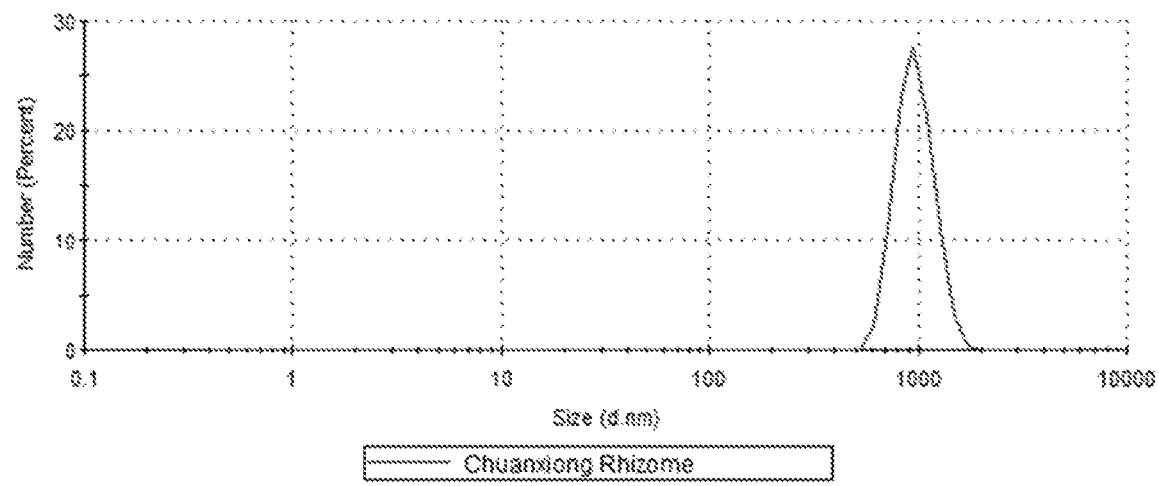
FIG. 2 shows the average particle size of milled suspension of Chuanxiong Rhizome prepared in accordance with an embodiment of the present invention.

Example 1—Preparation of Herbal Ingredient Capsule with Single-Herb Nano-Crystal Two grams of powder from Chuanxiong Rhizome were prepared with a benchtop milling machine (Tube Mill 100 control, IKA, Germany). The Chinese medicine powder was then dispersed in 18 g of distilled water with 4% poly(vinyl) alcohol (PVA). The resulting suspension (10% TCM content) was mixed with 20 g of zirconium oxide balls (00.5 mm) and wet milled at 800 RPM in zirconium oxide-made milling chamber (50 ml) with high energy ball mill (Emax, Retsch GmbH, Germany) for 150 minutes in a 15-minute milling/10-minute cool down cycle. The milled suspensions were separated with a sieve of 50 μm mesh size. Particle size analysis was performed using Zetasizer Nano ZS90 (Malvern Instruments, UK). The particles had an average size of about 980 nm (FIG. 2).

The TCM nanosuspension was dried by spray drying to obtain dried TCM nanocrystal powder with a laboratory scale spray dryer ADL311 (Yamato Scientific, Japan). The inlet temperature was measured to be 150° C., and the spray dried Chinese medicine nano-crystal was collected. The overall process yield of the dried Chinese medicine nanocrystal was 28.4%.

Chuanxiong Rhizome nano-crystals-containing capsule was fabricated by adding 2 g of the ball milled Chuanxiong Rhizome nano-crystals and 4 g of millet, into the coffee capsule. Forty milliliters of herbal decoction was successfully prepared from the capsule using coffee capsule machine, such as CMC-111 (German Pool Group Ltd, Hong Kong).

Example 2—Preparation of Multi-Herbal Nano-Crystals-Containing Capsule

Six grams of powders from Ziziphi spinosae Semen, Lycii Fructus, and Poria were separately prepared with a benchtop milling machine (Tube Mill 100 control, IKA, Germany).

Figure 3A:
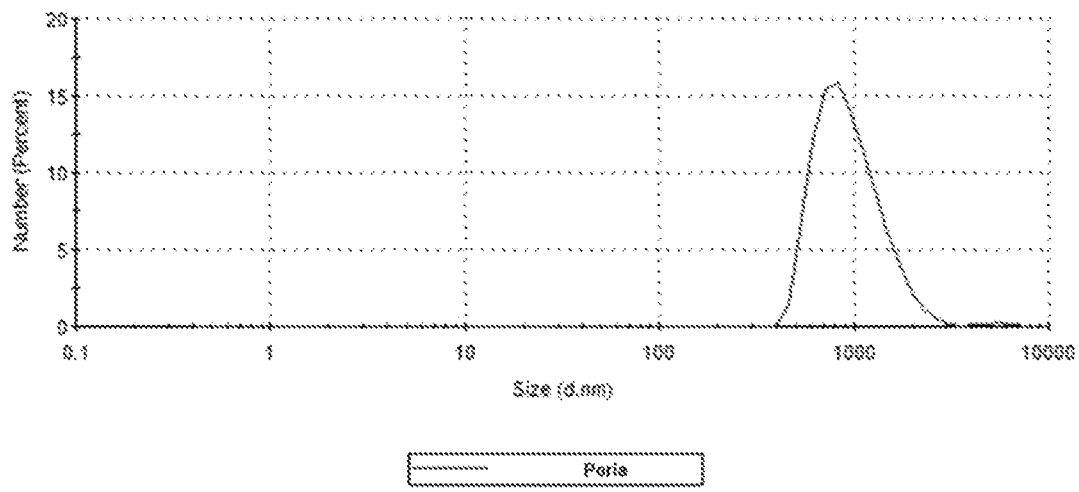
FIG. 3A shows an average particle sizes of milled suspensions of Poria prepared in accordance with an embodiment of the present invention.
Figure 3B:
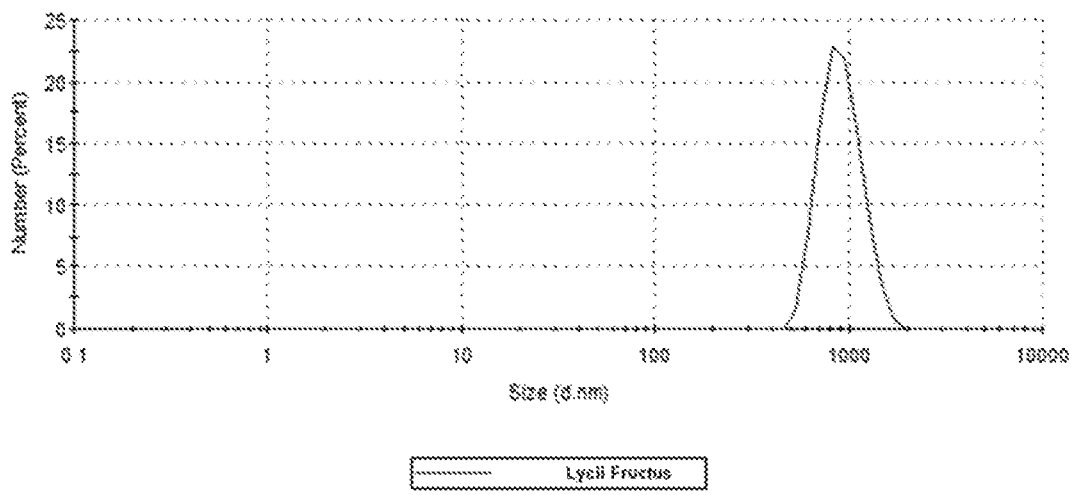
FIG. 3B shows an average particle sizes of milled suspensions of Lycii Fructus prepared in accordance with an embodiment of the present invention.
Figure 3C:
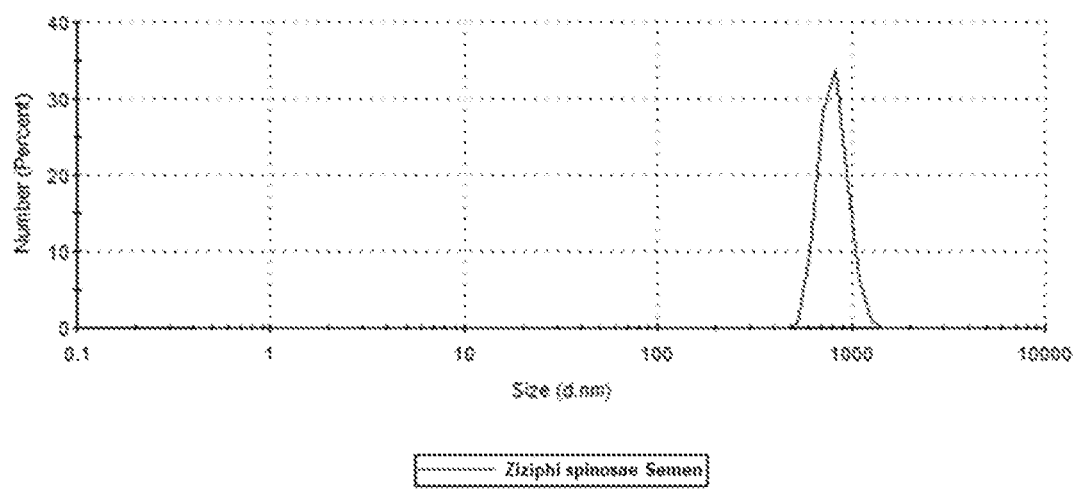
FIG. 3C shows an average particle sizes of milled suspensions of Ziziphi spinosae Semen prepared in accordance with an embodiment of the present invention.

The individual Chinese medicine powder was then dispersed in 54 g of distilled water with 1% poly(vinyl) alcohol (PVA). The resulting suspension (10% TCM content) was mixed with 60 g of zirconium oxide balls (00.5 mm) and wet milled at 1200 RPM in zirconium oxide-made milling chamber (150 ml) with high energy ball mill (Emax, Retsch GmbH, Germany) for 250 minutes in a 15-minute milling/10-minute cool down cycle. The milling temperature was controlled within 40° C. The milled suspensions were separated with sieve of 50 μm mesh size. Particle size analyses were performed using Zetasizer Nano ZS90 (Malvern Instruments, UK). The particles in milled suspensions of Ziziphi spinosae Semen, Lycii Fructus, Poria had average sizes of about 818 nm, 927 nm and 979 nm, respectively (FIGS. 3A-C).

The TCM nanosuspension was dried by spray drying to obtain dried TCM nano-crystal powder with a laboratory scale spray dryer ADL311 (Yamato Scientific, Japan). The inlet temperature was measured to be 150° C., and the spray dried Chinese medicine nano-crystals were collected. The overall process yield of the dried Chinese medicine nano-crystals ranged from 26.8 to 40.8%.

A multiple herbal ingredients-containing capsule was fabricated by adding 0.88 g of the ball milled Ziziphi spinosae Semen nano-crystal, 0.66 g of the ball milled Lycii Fructus nano-crystal, 0.44 g of ball milled Poria nano-crystal and 4 g of quinoa, into the coffee capsule. Forty milliliters of herbal ingredient capsule drink was successfully prepared from the capsule using coffee capsule machine, such as CMC-111 (German Pool Group Ltd, Hong Kong).

Figure 4:
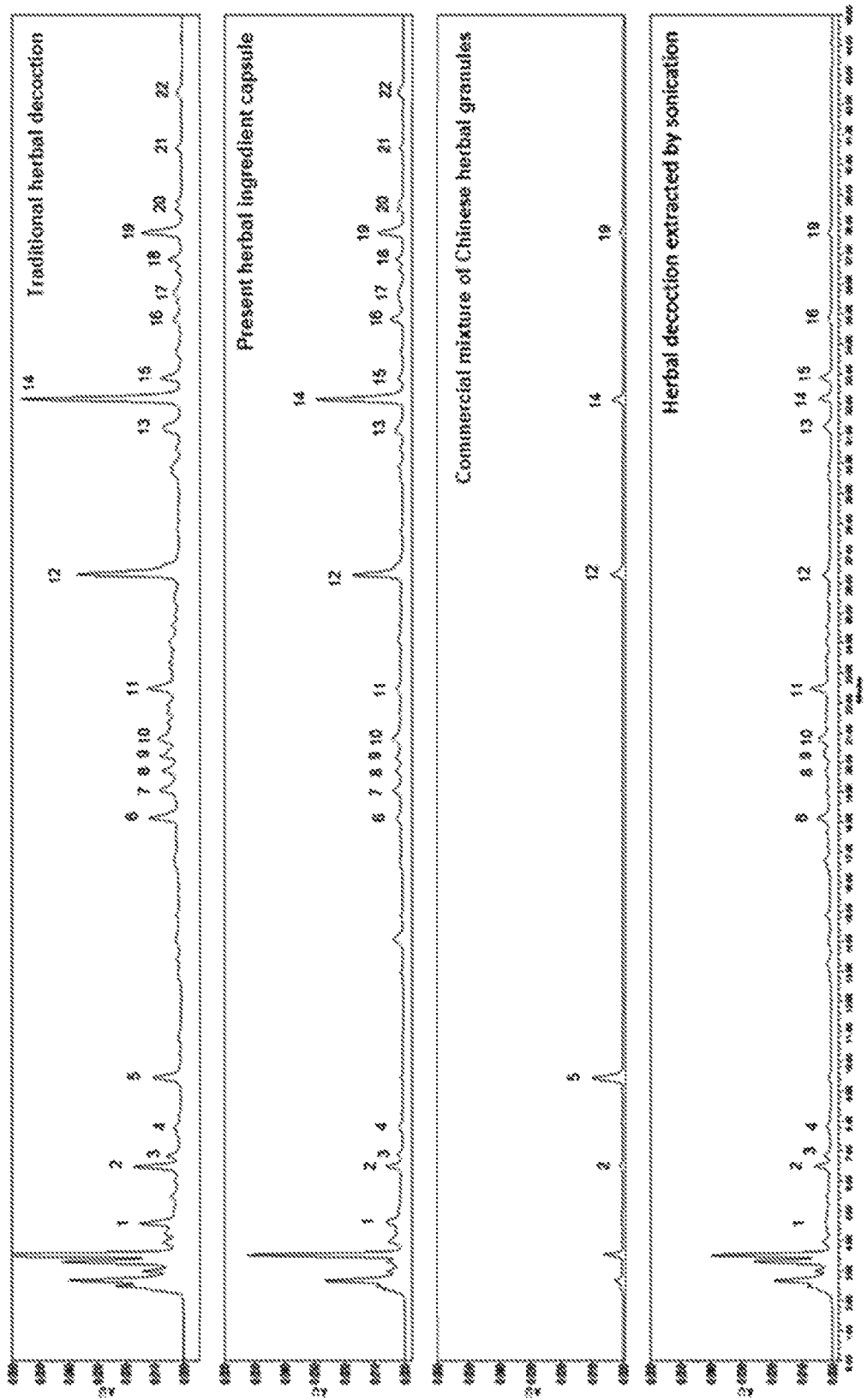
FIG. 4 shows a separated view of chromatographic fingerprints of the Chinese medicine decoctions prepared by traditional hour-long boiling of herbal ingredients, the present herbal ingredient capsule, a commercial mixture of Chinese herbal granules, and sonication of herbal ingredients.

Chromatographic fingerprints of the present herbal decoction, traditional herbal decoction and a commercial mixture of single herbal granules were obtained by HPLC (FIG. 4). The present herbal decoction (containing nano-crystals of Ziziphi spinosae Semen, Poria and Lycii Fructus in a weight ratio of 4:3:2) exhibited similarity in terms of its chromatographic fingerprint, comparing with that of traditional herbal decoction. On the other hand, only a few peaks were found in the commercial mixture of identical Chinese herbal granules. Also, the herbal ingredient capsule drink had demonstrated a higher yield and more peaks than the raw herb extracted in water under sonication for 1 hour. In FIG. 4, twenty-two peaks were identified in the traditional herbal decoction, where twenty-one of which could be identified in the present herbal decoction; whereas only five of which could be identified in the commercial mixture of identical Chinese herbal granules. Fifteen peaks could be identified in raw herb extracted by sonication, however, most of them are of smaller intensities, comparing with that of the herbal ingredient capsule drink. The results show that the present herbal decoction prepared as described in Example 2 is capable to increase the saturation solubility as well as the dissolution rate, when comparing with the commercial mixture of identical Chinese ingredient granules or extraction by sonication.

Figure 5:
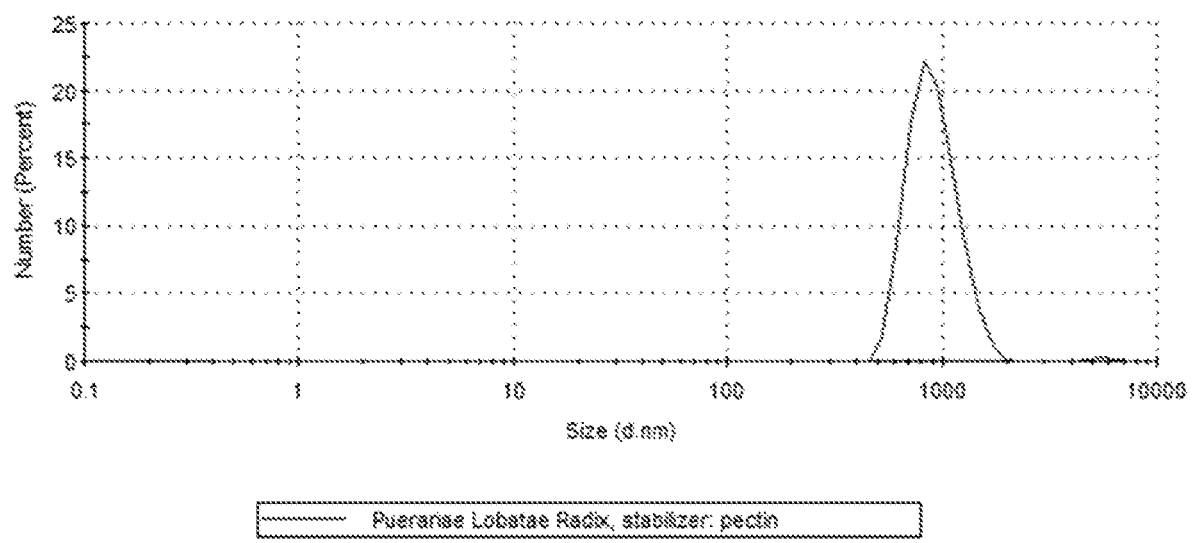
FIG. 5 shows an average particle size of milled suspension of Puerariae Lobatae Radix prepared in accordance with an embodiment of the present invention.

Example 3—Preparation of Herbal Ingredient Capsule with Single-Herb Nanocrystal with Non-Ionic Stabilizing Agent Three grams of powder from Puerariae Lobatae Radix were prepared with a benchtop milling machine (Tube Mill 100 control, IKA, Germany). The Chinese medicine powder was then mixed with 30 mg of pectin and dispersed in 20 g of distilled water. The resulting suspension (13% TCM content) was mixed with 60 g of zirconium oxide balls (00.5 mm) and wet milled at 1200 RPM in zirconium oxide-made milling chamber (50 ml) with high energy ball mill (Emax, Retsch GmbH, Germany) for 180 minutes in a 30-minute milling/15-minute cool down cycle. The milled suspensions were separated with sieve of 50 μm mesh size. Particle size analysis was performed using Zetasizer Nano ZS90 (Malvern Instruments, UK). The particles had an average size of 959 nm (FIG. 5).

The TCM nanosuspension was dried by freeze drying to obtain dried TCM nanocrystal powder with a laboratory scale VirTis BenchTop Pro freeze dryers (SP Scientific, NY, US). The freeze dried Chinese medicine nanocrystal was collected. The overall process yield of the dried Chinese medicine nano-crystals was 54%.

A Puerariae Lobatae Radix nano-crystals-containing capsule was fabricated by adding 1 g of the ball milled Puerariae Lobatae Radix nano-crystals and 2.5 g of quinoa, into the coffee capsule. Twenty milliliters of herbal decoction was successfully prepared from the capsule using coffee capsule machine, such as CMC-111 (German Pool Group Ltd, Hong Kong).

Figure 6:
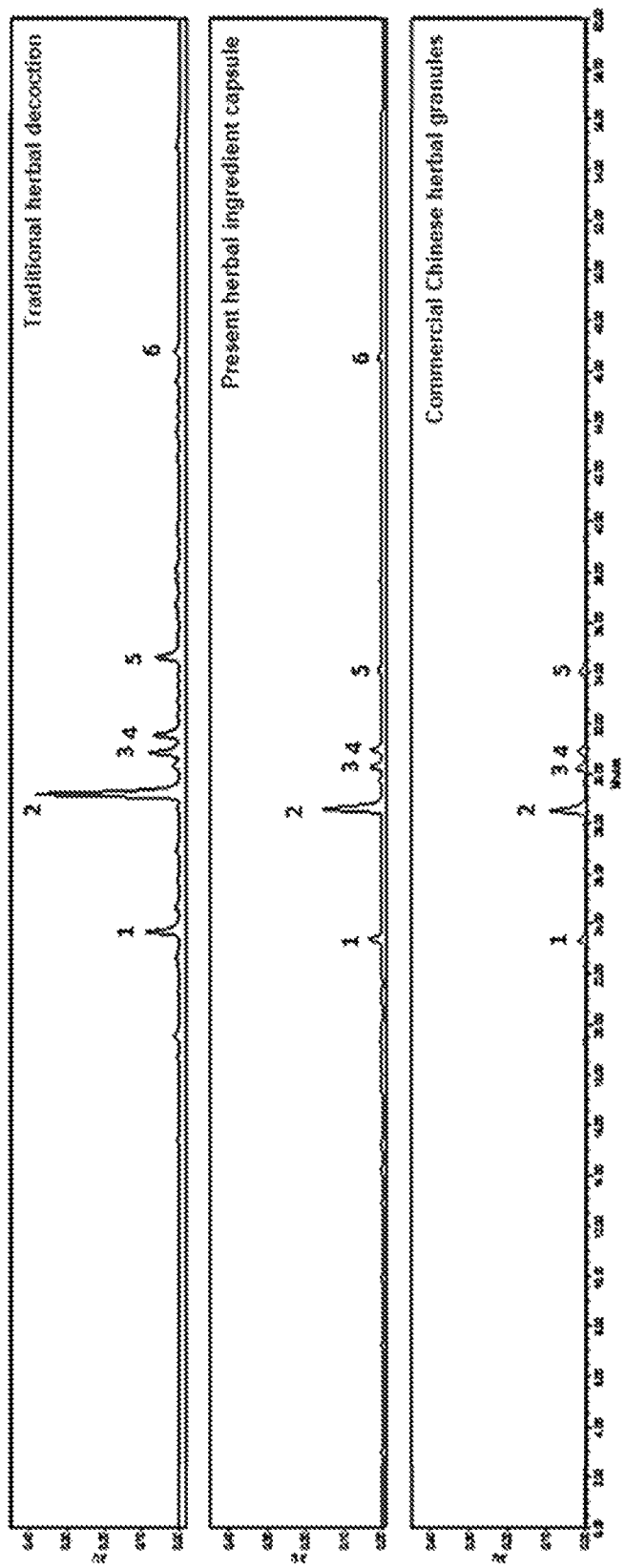
FIG. 6 shows a separated view of chromatographic fingerprints of Puerariae Lobatae Radix decoctions prepared by traditional hour-long boiling of herbal ingredients, the present herbal ingredient capsule, and commercial Chinese herbal granules.

Chromatographic fingerprints of the present herbal decoction, traditional herbal decoction and a commercial herbal granules were obtained by HPLC (FIG. 6). Herbal ingredient capsule drink exhibited similarity in terms of its chromatographic fingerprint, comparing with that of traditional herbal decoction. On the other hand, only a few peaks were found in the commercial Chinese herbal granules. In FIG. 6, six peaks were identified in the traditional herbal decoction, and all of which could be identified in the present herbal decoction; whereas only five of which could be identified in the commercial Chinese herbal granules. However, most of them are of smaller intensities, comparing with that of the present herbal decoction. The results show that the present herbal decoction prepared as described in Example 3 is capable to increase the saturation solubility as well as the dissolution rate, when comparing with the commercial Chinese ingredient granules.

Figure 7:
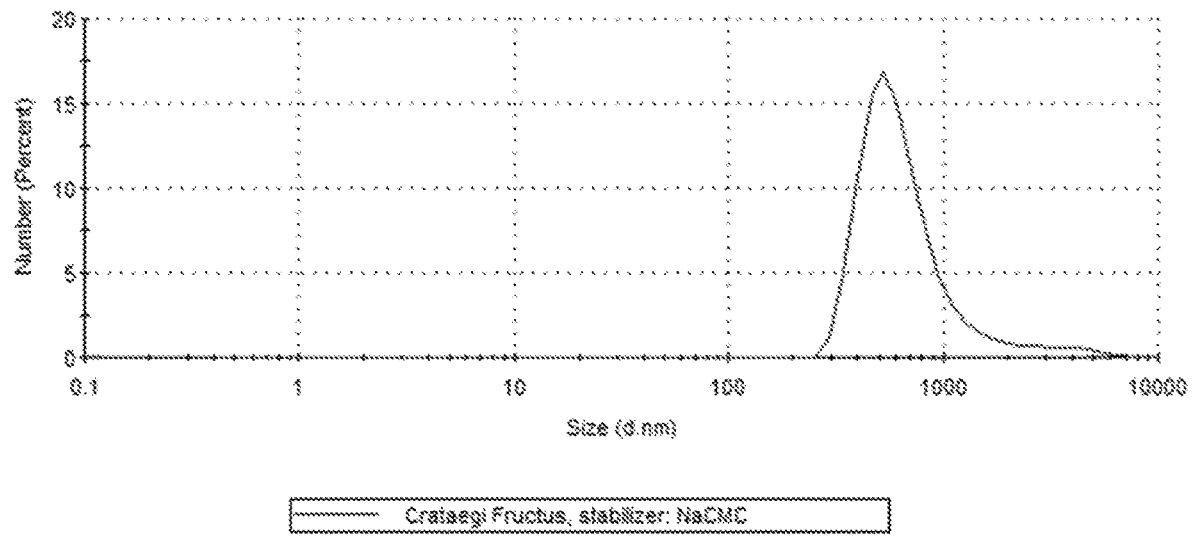
FIG. 7 shows an average particle size of milled suspension of Crataegi Fructus prepared in accordance with an embodiment of the present invention.

Example 4—Preparation of Single Herbal Nano-Crystal-Containing Capsule with Ionic Stabilizing Agent Two grams of powder from Crataegi Fructus were prepared with a benchtop milling machine (Tube Mill 100 control, IKA, Germany). The Chinese medicine powder was then mixed with 80 mg of sodium carboxymethylcellulose and dispersed in 25 g of distilled water. The resulting suspension (7% TCM content) was mixed with 60 g of zirconium oxide balls (00.5 mm) and wet milled at 1200 RPM in zirconium oxide-made milling chamber (50 ml) with high energy ball mill (Emax, Retsch GmbH, Germany) for 180 minutes in a 30-minute milling/15-minute cool down cycle. The milled suspensions were separated with a sieve of 50 μm mesh size. Particle size analysis was performed using Zetasizer Nano ZS90 (Malvern Instruments, UK). The particles had an average size of 762 nm (FIG. 7).

The TCM nanosuspension was dried by freeze drying to obtain dried TCM nanocrystal powder with a laboratory scale VirTis BenchTop Pro freeze dryers (SP Scientific, NY, US). The freeze dried Chinese medicine nanocrystal was collected. The overall process yield of the dried Chinese medicine nanocrystal was 55%.

Crataegi Fructus capsule was fabricated by adding 1 g of the ball milled Crataegi Fructus nanocrystal and 2.5 g of natural spacer, into the coffee capsule. Twenty milliliters of herbal ingredient capsule drink was successfully prepared from the capsule using coffee capsule machine, such as CMC-111 (German Pool Group Ltd, Hong Kong).

Figure 8:
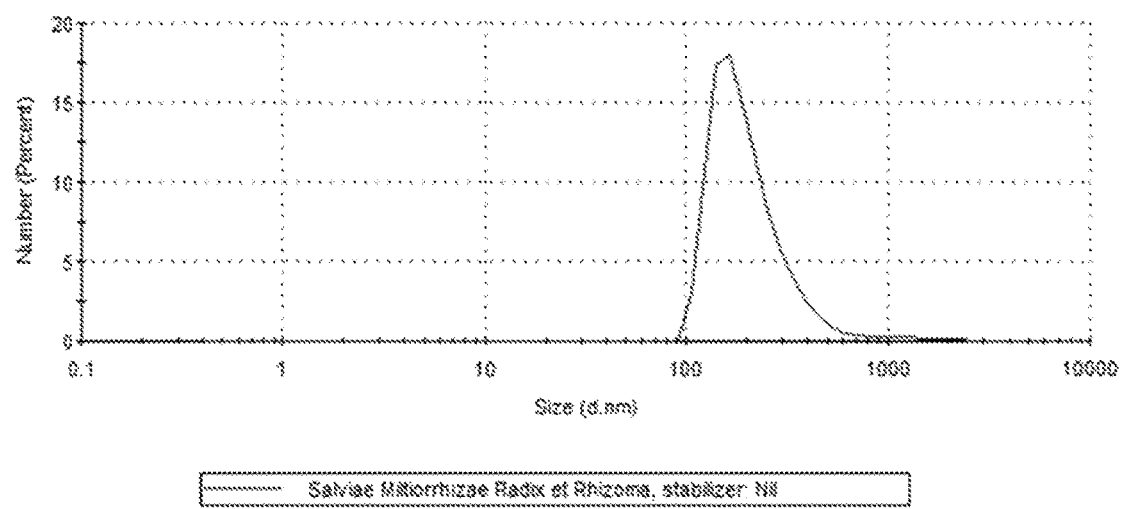
FIG. 8 shows an average particle size of milled suspension of Salviae miltiorrhizae Radix et Rhizoma prepared in accordance with an embodiment of the present invention.

Example 5—Preparation of Single-Herbal Nanocrystal-Containing Capsule without any Stabilizing Agent Three grams of powder from Salviae Miltiorrhizae Radix et Rhizoma were prepared with a benchtop milling machine (Tube Mill 100 control, IKA, Germany). The Chinese medicine powder was then dispersed in 20 g of distilled water. The resulting suspension (13% TCM content) was mixed with 60 g of zirconium oxide balls (Ø0.5 mm) and wet milled at 1200 RPM in zirconium oxide-made milling chamber (50 ml) with high energy ball mill (Emax, Retsch GmbH, Germany) for 180 minutes in a 30-minute milling/15-minute cool down cycle. The milled suspensions were separated with sieve of 50 μm mesh size. Particle size analysis was performed using Zetasizer Nano ZS90 (Malvern Instruments, UK). The particles had an average size of 220 nm (FIG. 8).

The TCM nanosuspension was dried by freeze drying to obtain dried TCM nanocrystal powder with a laboratory scale VirTis BenchTop Pro freeze dryers (SP Scientific, NY, US). The freeze dried Chinese medicine nanocrystal was collected. The overall process yield of the dried Chinese medicine nanocrystal was 65%.

Salviae Miltiorrhizae Radix et Rhizoma capsule was fabricated by adding 1 g of the ball milled Salviae Miltiorrhizae Radix et Rhizoma nanocrystal into the coffee capsule. Twenty milliliters of herbal ingredient drink was successfully prepared from the herbal nanocrystal by direct dissolution in water of 80° C. with stirring.

Figure 9:
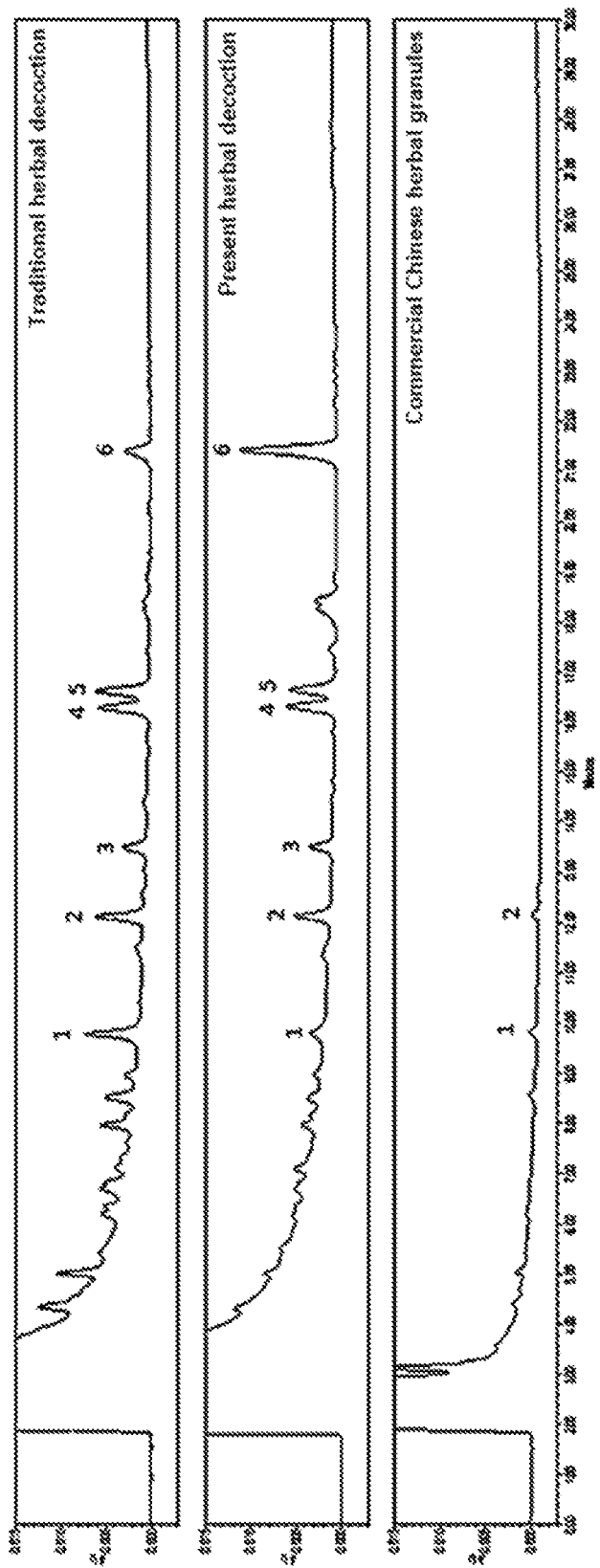
FIG. 9 shows a separated view of chromatographic fingerprints of Salviae miltiorrhizae Radix et Rhizoma decoctions prepared by traditional hour-long boiling of herbal ingredients, the present herbal ingredient capsule and commercial Chinese herbal granules.

Chromatographic fingerprints of the present herbal decoction, traditional herbal decoction and commercial Chinese herbal granules were obtained by HPLC (FIG. 9). The present herbal decoction exhibited similarity in terms of its chromatographic fingerprint, comparing with that of traditional herbal decoction. On the other hand, only a few peaks were found in the commercial Chinese herbal granules. In FIG. 9, six peaks were identified in the traditional herbal decoction, and all of which could be identified in the herbal ingredient drink; whereas only two of which could be identified in the commercial Chinese herbal granules. However, most of them are of smaller intensities, comparing with that of the present herbal decoction. The results show that the present herbal decoction prepared as described in Example 5 is capable to increase the saturation solubility as well as the dissolution rate, when comparing with the commercial Chinese ingredient granules.

Figure 10:
FIG. 10 shows a broken capsule due to the excessive water pressure accumulation caused by the absence of the non-additive and anti-caking spacers.

Comparative Example 1—Preparation of Herbal Ingredient Capsule with Multi-Herb Nanocrystals without the Non-Additive and Anti-Caking Spacers Multi-herbal ingredient-containing capsule was fabricated under the same condition as Example 2 without the addition of any natural or synthetic spacer, by incorporating nano-crystals of the multiple nano-cyrstallized herbal ingredients into the coffee capsule. Only 7 milliliters of herbal ingredient capsule drink was eluted from the capsule using coffee capsule machine CMC-111 (German Pool Group Ltd, Hong Kong). Due to the ineffective flow of water without the spacer, the capsule was broken by the excessive water pressure. Dry powder was found inside the used capsule, which further confirms the ineffective flow of water due to the absence of the spacer (FIG. 10).

Example 2 and Comparative Example 1

Example 2 and Comparative Example 1 use the same compositions and amounts of herbal nanocrystal. However, the addition of the natural spacer in Example 2 remarkably improves the water flow for a full access to all herbal nanocrystals. Example 2 also maintains the pressure inside the capsule by protecting its integrity during processing or brewing by the food processor, and gives an herbal decoction with sufficient volume and active ingredient for normal consumption.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

INDUSTRIAL APPLICABILITY

The present invention does not only apply to traditional Chinese medicine but also some beverages that are poorly soluble or substantially insoluble in the commonly used solvent. The introduction of spacers into the composition for the present herbal decoction to facilitate dispersion of the nano-crystals of the food active ingredients while avoiding caking of the food or beverage ingredients during processing or brewing could also widen the variety of food or beverage active ingredients and/or additives to be added into similar kind of package for use in food processor. The cost, time and process of preparing the food or beverage active ingredients from the raw materials into a ready-to-use instant food or beverage product can also be significantly lowered/shortened/simplified.

REFERENCE

The following references are incorporated herein by reference in their entirety:
1. Shang E, Zhu Z, Liu L, Tang Y, Duan J A., "UPLC-QTOF-MS with chemical profiling approach for rapidly evaluating chemical consistency between traditional and dispensing granule decoctions of Tao-Hong-Si-Wu decoction", *Chem Cent J.*, 2012 Nov. 24; 6(1):143.
2. Zhang Q, Wang C H, Ma Y M, Zhu E Y, Wang Z T., "UPLC-ESI/MS determination of 17 active constituents in two categorized formulas of traditional Chinese medicine, Sanhuang Xiexin Tang and Fuzi Xiexin Tang: application in comparing the differences in decoctions and macerations", *Biomed Chromatogr.*, 2013 August; 27(8): 1079-88.
3. Rabinow B E., "Nanosuspensions in drug delivery", *Nat Rev Drug Discov.*, 2004 September; 3(9):785-96.
4. George M, Ghosh I., "Identifying the correlation between drug/stabilizer properties and critical quality attributes (CQAs) of nanosuspension formulation prepared by wet media milling technology", *Eur J Pharm Sci.*, 2013 Jan. 23; 48(1-2): 142-52.
5. Loh Z H, Samanta A K, Heng, P W S., "Overview of milling techniques for improving the solubility of poorly water-soluble drugs", *Asian Journal of Pharmaceutical Sciences*, 2015; 10(4):255-274.
6. Goldberg M1, Langer R, Jia X., "Nanostructured materials for applications in drug delivery and tissue engineering", J Biomater Sci Polym Ed. 2007; 18(3):241-68.
7. Vogt M, Kunath K, Dressman J B., "Dissolution enhancement of fenofibrate by micronization, cogrinding and spray-drying: comparison with commercial preparations", *Eur J Pharm Biopharm.* 2008 February; 68(2):283-8.
8. CN103211759B: "Puerarin nanocrystalline medical composition and preparation method thereof", Institute of Pharmacology and Toxicology, The Academy of Military Medical Sciences; Mar. 28, 2013
9. CN102895451A: "Preparation technology and production method for integrated new formulation of expelling stasis below the diaphragm decoction", Suzhou Zhiweitang Biotechnology Co., Ltd; Yang Hongshu; Jul. 29, 2011

The invention claimed is:

1. A nano-crystallized herbal ingredient-containing package for use in a food processor or being used directly to prepare an herbal decoction, said package comprising:
    a housing comprising at least a side wall, a top wall and a bottom wall which forms a cavity;
    single or multiple herbal ingredient nano-crystals having an average particle size of equal to or less than 1,000 nm at about 5-50 wt. % to the total weight of components inside the cavity of the housing;
    one or more non-additive and anti-caking spacers having an average particle size of about 0.5 to 5 mm at about 45-90 wt. % to the total weight of components inside the cavity of the housing for preventing the nano-crystals from caking thereby permitting solvent to flow through the package towards said single or multiple herbal ingredient nano-crystals during processing by the food processor; and
    one or more stabilizing agents at about 0-5 wt. % for stabilizing said single or multiple herbal ingredient nano-crystals during nano-crystallization of the herbal ingredients and during preparation of said herbal decoction.

2. The package according to claim 1, wherein the housing is made of polymer, metal and/or an alloy thereof.

3. The package according to claim 1, wherein the housing further comprises an internal porous structure made of polymers and/or fibers.

4. The package according to claim 1, wherein said single or multiple herbal ingredient nano-crystals are prepared by ultrafine grinding or high-pressure pulverisation of raw or coarse herbal material.

5. The package according to claim 1, wherein said single or multiple herbal ingredient nano-crystals comprises:
    nano-crystals of part of the flower, leaf, seed, fruit, stem, root and rhizome of species under kingdom Plantae; and/or
    nano-crystals of part of cap, stalk, hyphae and spores of species under kingdom Fungi.

6. The package according to claim 1, wherein said single or multiple herbal ingredient nano-crystals comprise nano-crystals of one or more of Chuanxiong Rhizome, Poria, Lycii Fructus, Ziziphi spinosae Semen, Puerariae Lobatae Radix, Crataegi Fructus, and/or Salviae miltiorrhizae Radix et Rhizoma.

7. The package according to claim 1, wherein the one or more stabilizing agents comprise one or more ionic stabilizing agents and/or one or more non-ionic stabilizing agents.

8. The package according to claim 7, wherein said one or more ionic stabilizing agents comprise sodium carboxymethylcellulose, sodium lauryl sulfate, and/or dioctyl sodium sulfosuccinate.

9. The package according to claim 7, wherein said one or more non-ionic stabilizing agents comprise poly(vinyl) alcohol, D-alpha-tocopheryl polyethylene glycol succinate, pectin, and/or hydroxypropylmethyl cellulose.

10. The package according to claim 1, wherein the one or more non-additive and anti-caking spacers comprise natural and/or synthetic materials.

11. The package according to claim 10, wherein said natural material comprises one or more of sesame, millet, and/or quinoa.

12. The package according to claim 10, wherein said synthetic material comprises one or more of amorphous silica, and/or zirconium oxide beads.

13. The package according to claim 1, wherein the average particle size of said one or more non-additive and anti-caking spacers is about 1 mm to 3 mm.

14. The package according to claim 1, wherein said solvent is about 75 to 100° C.

15. The package according to claim 1, wherein said package is selected from capsule, cartilage, pod, bag, and container in any three-dimensional shape.

16. A method of preparing an herbal decoction from the package according to claim 1, said method comprising:
    providing the nano-crystallized herbal ingredient-containing package of claim 1;
    providing a flow of solvent under a pressure of 1.01325 to 20 bar and temperature of about 75 to 100° C. to said package such that the solvent flows through an opening of said package towards single or multiple herbal ingredient nano-crystals in order to process or brew for a first period of time; or
    providing solvent under atmospheric pressure and at a temperature of about 75 to 100° C. to said package for a second period of time until the solvent at least partially dissolves said single or multiple herbal ingredient nano-crystals.

17. The method according to claim 16, wherein the flow of said solvent is generated by a food processor.

18. The method according to claim 16, wherein said first period of time is equal to or less than a minute.

19. The method according to claim 16, wherein said second period of time is no more than 20 minutes.

* * * * *